US008513193B2

(12) United States Patent
Rosier et al.

(10) Patent No.: US 8,513,193 B2
(45) Date of Patent: Aug. 20, 2013

(54) PROTECTING AND REPAIRING CARTILAGE AND MUSCULOSKELETAL SOFT TISSUES

(75) Inventors: Randy N. Rosier, Rochester, NY (US); Michael J. Zuscik, North Chili, NY (US); Erik Sampson, Rochester, NY (US); Susan V. Bukata, Pittsford, NY (US); J. Edward Puzas, Pittsford, NY (US); Hani Awad, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/124,002

(22) PCT Filed: Oct. 13, 2009

(86) PCT No.: PCT/US2009/060499
§ 371 (c)(1),
(2), (4) Date: May 20, 2011

(87) PCT Pub. No.: WO2010/045229
PCT Pub. Date: Apr. 22, 2010

(65) Prior Publication Data
US 2012/0021986 A1 Jan. 26, 2012

Related U.S. Application Data

(60) Provisional application No. 61/104,942, filed on Oct. 13, 2008.

(51) Int. Cl.
*A61K 39/29* (2006.01)
*A61K 38/00* (2006.01)
*A61K 38/16* (2006.01)

(52) U.S. Cl.
USPC .................. 514/11.8; 514/17.1; 514/21.3

(58) Field of Classification Search
None
See application file for complete search history.

(56) References Cited

U.S. PATENT DOCUMENTS

| 5,846,931 A | 12/1998 | Hattersley et al. |
| 6,787,518 B1 | 9/2004 | Kato et al. |

FOREIGN PATENT DOCUMENTS

| JP | 2005247768 A | 9/2005 |
| WO | 95/11697 A1 | 5/1995 |
| WO | 98/44925 A1 | 10/1998 |
| WO | 03/026689 A1 | 4/2003 |
| WO | 2007/003958 A2 | 1/2007 |
| WO | 2007/118680 A2 | 10/2007 |
| WO | 2009/047361 A2 | 4/2009 |

OTHER PUBLICATIONS

Sondergaard et al. 2008 Osteoarthritis and Cartilage 16(s4):S81-S82, published Sep. 2008.*
Sondergaard et al. Sep. 2008. Journal of Bone and Mineral Res. 23(Suppl S):S412.*
http://www.drweil.com/drw/u/ART00662/osteoarthritis-treatment, downloaded Dec. 21, 2012.*
Adams et al., "Integration of signaling pathways regulating chondrocyte differentiation during endochondral bone formation," J. Cellular Physiology 213(3):635-41 (2007).
Anandacoomarasamy et al., "Predictors of clinical response to intra-articular Hylan injections—a prospective study using synovial fluid measures, clinical outcomes, and magnetic resonance imaging," J. Rheumatology 35(4):685-90 (2008).
Bahrami et al., "Endochondral ossification of costal cartilage is arrested after chondrocytes have reached hypertrophic stage of late differentiation," Matrix Biol. 19(8):707-15 (2001).
Barnes et al., "Stimulation of fracture-healing with systemic intermittent parathyroid hormone treatment," J. Bone Joint Surgery 90S:120-7 (2008).
Bruyere and Reginster, "Glucosamine and chondroitin sulfate as therapeutic agents for knee and hip osteoarthritis," Drugs and Aging 24(7):573-80 (2007).
Buckwalter et al., "Articular cartilage and osteoarthritis," Instructional Course Lectures 54:465-80 (2005).
Crabb et al., "Differential effects of parathyroid hormone on chick growth plate and articular chondrocytes," Calcified Tiss. Int. 50:61-6 (1992).
Drissi et al., "Transcriptional regulation of chondrocyte maturation: potential involvement of transcription factors in OA pathogenesis," Molecular Aspects of Medicine 26(3):169-79 (2005).
Felson and Kim, "The futility of current approaches to chondroprotection," Arthritis & Rheumatism 56(5):1378-83 (2007).
Gaissmaier et al., "Growth and differentiation factors for cartilage healing and repair," Injury 39(1):S88-96 (2008).
Garstang and Stitik, "Osteoarthritis: Epidemiology, Risk Factors, and Pathophysiology," Physical Medicine and Rehabilitation 85(11) Supplement (2006).
Gomez-Barrena et al., "Sequential changes of parathyroid hormone related protein (PTHrP) in articular cartilage during progression of inflammatory and degenerative arthritis," Annals of the Rheumatic Diseases 63(8):917-22 (2004).
Kawaguchi, "Endochondral ossification signals in cartilage degradation during osteoarthritis progression in experimental mouse models," Molecules & Cells 25(1):1-6 (2008).
Lanske et al., "PTH/PTHrP receptor in early development and Indian hedgehog-regulated bone growth," Science 273 (5275):663-6 (1996).
Loveys et al., "Effects of parathyroid hormone-related peptide on chick growth plate chondrocytes," J. Orthop. Res. 11 (6):884-91 (1994).
Miller et al., "Longterm reduction of back pain risk in women with osteoporosis treated with teriparatide compared with alendronate," J. Rheumatology 32(8):1556-62 (2005).
NPS Pharmaceuticals, "2007 Annual report," (2007).

(Continued)

*Primary Examiner* — Shulamith H Shafer
(74) *Attorney, Agent, or Firm* — Kilpatrick, Townsend & Stockton LLP

(57) ABSTRACT

Provided herein are compositions and methods related to promoting protection or repair of articular cartilage and/or musculoskeletal soft tissue by contacting the cartilage, tissues or cellular components thereof with a parathyroid hormone/parathyroid hormone-related protein (PTH/PTHrP) receptor agonist or releasing factor.

3 Claims, 14 Drawing Sheets

(56) References Cited

OTHER PUBLICATIONS

Okano et al., "Expression of parathyroid hormone-related peptide in human osteoarthritis," J. Orthopaedic Research 15 (2):175-80 (1997).

Pazianas et al., "Intestinal failure-associated metabolic bone diseases and response to teriparatide," Nutr. Clin. Pract. 21(6):605-9 (2006).

Schipani and Provot, "PTHrP, PTH, and the PTH/PTHrP receptor in endochondral bone development," Birth Defects Research. Part C, Embryo Today:Reviews 69(4):352-62 (2003).

Vortkamp et al., "Regulation of rate of cartilage differentiation by Indian hedgehog and PTH-related protein," Science 273(5275):613-22 (1996).

Supplementary European Search Report for EP 09821118, completed Jul. 30, 2012.

* cited by examiner

Sham 4 weeks

Mild Injury 4 weeks

Severe Injury 4 weeks

Severe Injury + PTH 4 weeks

Sham 12 weeks

Mild Injury 12 weeks

Severe Injury 12 weeks

Severe Injury + PTH 12 weeks

SEQUENCE LISTING

```
<160> NUMBER OF SEQ ID NOS: 3

<210> SEQ ID NO 1
<211> LENGTH: 115
<212> TYPE: PRT
<213> ORGANISM: Homo sapiens
<220> FEATURE:
<223> OTHER INFORMATION: Parathyroid Hormone

<400> SEQUENCE: 1

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30

Val Ser Glu Ile Gln Leu Met His Asn Leu Gly Lys His Leu Asn Ser
        35                  40                  45

Met Glu Arg Val Glu Trp Leu Arg Lys Lys Leu Gln Asp Val His Asn
    50                  55                  60

Phe Val Ala Leu Gly Ala Pro Leu Ala Pro Arg Asp Ala Gly Ser Gln
65                  70                  75                  80
```

-continued

```
Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln
        115

<210> SEQ ID NO 2
<211> LENGTH: 177
<212> TYPE: PRT
<213> ORGANISM: Homo sapiens
<220> FEATURE:
<223> OTHER INFORMATION: Parathyroid hormone related peptide

<400> SEQUENCE: 2

Met Gln Arg Arg Leu Val Gln Gln Trp Ser Val Ala Val Phe Leu Leu
  1               5                  10                  15

Ser Tyr Ala Val Pro Ser Cys Gly Arg Ser Val Glu Gly Leu Ser Arg
             20                  25                  30

Arg Leu Lys Arg Ala Val Ser Glu His Gln Leu Leu His Asp Lys Gly
         35                  40                  45

Lys Ser Ile Gln Asp Leu Arg Arg Phe Phe Leu His His Leu Ile
     50                  55                  60

Ala Glu Ile His Thr Ala Glu Ile Arg Ala Thr Ser Glu Val Ser Pro
 65                  70                  75                  80

Asn Ser Lys Pro Ser Pro Asn Thr Lys Asn His Pro Val Arg Phe Gly
                 85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 3
<211> LENGTH: 34
<212> TYPE: PRT
<213> ORGANISM: Homo sapiens
<220> FEATURE:
<223> OTHER INFORMATION: Parathyroid Hormone

<400> SEQUENCE: 3

Met Ile Pro Ala Lys Asp Met Ala Lys Val Met Ile Val Met Leu Ala
  1               5                  10                  15

Ile Cys Phe Leu Thr Lys Ser Asp Gly Lys Ser Val Lys Lys Arg Ser
             20                  25                  30

Val Ser
```

PROTECTING AND REPAIRING CARTILAGE AND MUSCULOSKELETAL SOFT TISSUES

CROSS-REFERENCE TO RELATED APPLICATION

This application claims the benefit of U.S. Provisional Application No. 61/104,942, filed Oct. 13, 2008.

STATEMENT REGARDING FEDERALLY FUNDED RESEARCH

This invention was made with government support under Grant Nos. 5P50AR054041 and AR045700 awarded by the National Institutes of Health. The government has certain rights in the invention.

BACKGROUND

There is currently no known medical treatment for stimulating the protection or repair of cartilage, tendons, muscles, meniscus, intervertebral discs, or ligaments. Osteoarthritis, for example, which is associated with degeneration of articular cartilage, is a leading cause of disability and immobility, with current estimates of over 40 million Americans affected. Articular cartilage in adults has an extremely limited ability to repair itself, and once deterioration begins, the outcome is usually an irreversible progressive degeneration and associated inflammation, pain and dysfunction. Current treatments include anti-inflammatory and pain medications, injections of steroids and hyaluronic acid into the affected joint, and surgeries, such as total joint replacement. Oral supplements of glucosamine and chondroitin sulfate have been proposed as chondroprotective, but the chondroprotective effects of such oral supplements are controversial and minimal at best.

SUMMARY

Provided herein are in vivo and in vitro methods of promoting protection or repair of articular cartilage and/or musculoskeletal soft tissue (e.g., non-articular cartilage like meniscal cartilage, intervertebral disc, skeletal muscle, tendon, or ligament) using a parathyroid hormone/parathyroid hormone-related protein (PTH/PTHrP) receptor agonist or releasing agent, For example, provided herein is a method of promoting protection or repair of articular cartilage and/or musculoskeletal soft tissue in a subject comprising selecting a subject in need of such protection or repair and administering intermittently to the subject a PTH/PTHrP receptor agonist. Also provided is a method of protecting or promoting repair of articular cartilage and/or musculoskeletal soft tissue in a subject comprising selecting a subject in need of protection or repair of articular cartilage and administering intermittently to the subject a parathyroid hormone releasing factor.

DESCRIPTION OF DRAWINGS

FIG. 4 shows micrographs of articular cartilage in mice with a murine knee injury model (mild injury and severe injury) and sham mice at 4, 8, and 12 weeks following surgery and with 4, 8, or 12 weeks of daily treatment with teriparatide (+PTH).

FIG. 7A shows images of micrographs demonstrating that proteoglycan production is stimulated by treatment with teriparatide and PTH for 4 weeks following surgery. FIG. 7B shows a histogram quantifying the Alcian Blue staining intensity demonstrating an increase in proteoglycan production following treatment with teriparatide and PTH for 4 weeks following surgery.

FIG. 8A shows images of micrographs demonstrating that treatment with teriparatide and PTH for 12 weeks reduces the amount of cartilage loss following surgery. FIG. 8B shows a histogram quantifying the normalized cartilage area following treatment with teriparatide and PTH for 12 weeks following surgery. Treatment with teriparatide or PTH reduces the amount of cartilage loss as compared to treatment with saline.

FIG. 9A shows images of micrographs demonstrating that treatment with teriparatide and PTH for 4 weeks after an 8 week delay post surgery reduces the amount of cartilage loss as compared to treatment with saline. FIG. 9B shows a histogram quantifying the normalized cartilage area following treatment with teriparatide and PTH for 4 weeks after an 8 week delay post surgery. Delayed treatment with teriparatide or PTH reduces the amount of cartilage loss as compared to treatment with saline.

FIG. 12A shows a micrograph of a white zone tear in a rabbit meniscus treated with saline for 4 weeks as a control. FIG. 12B shows a micrograph of a white zone tear in a rabbit meniscus treated daily with teriparatide for 4 weeks. Treatment with teriparatide shows narrowing of the defect with increased cellularity and proteoglycan content consistent with a stimulatory healing effect on the meniscus.

DETAILED DESCRIPTION

Figure 1:
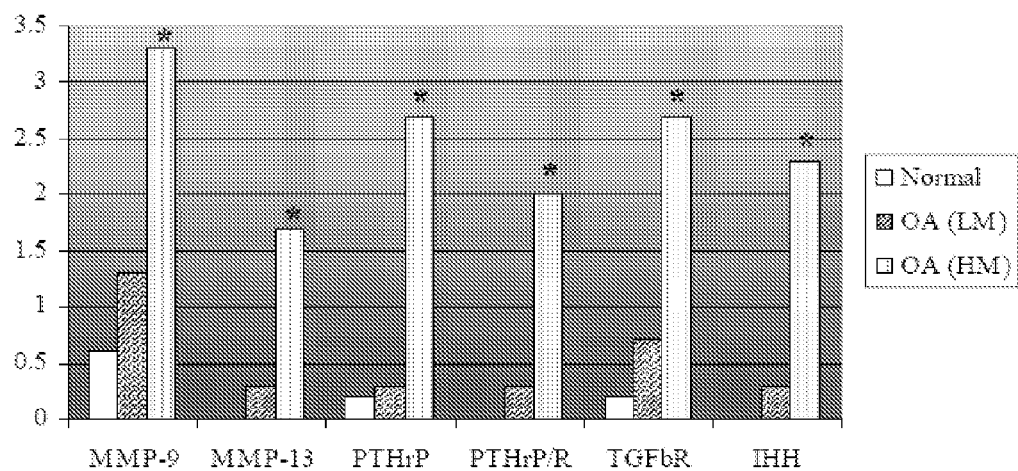
FIG. 1 is a histogram showing the immunohistochemical detection levels of various maturational markers (matrix metalloproteinase 9 (MMP9), matrix metalloproteinase 13 (MMP13), parathyroid hormone-related protein (PTHrP), parathyroid hormone/parathyroid hormone-related protein receptor (PTHrP/R), transforming growth factor β receptor (TGFβR), and Indian hedgehog (IHH)) in cartilage of normal subjects and in subjects with mild (OA(LM) and severe osteoarthritis (OA(HM)).

The parathyroid hormone/parathyroid hormone-related protein (PTH/PTHrP) receptor, also known as the Type 1 PTH receptor (PTHR1), is not expressed in normal adult articular cartilage but is expressed in chondrocytes early in the degenerative process. PTH/PTHrP receptor expression occurs in cartilage as part of normal endochondral bone formation and in the cartilaginous growth plates of children. The receptor and its ligands (PTH and PTHrP) regulate endochondral ossification, in which cartilage mineralizes and forms bone. PTHrP stimulates growth plate chondrocyte proliferation and proteoglycan synthesis. In addition to stimulating cell proliferation and matrix synthesis by growth plate chondrocytes, PTH and PTHrP inhibit the subsequent events of the endochondral ossification cellular program, which include cellular hypertrophy, expression of matrix-degrading enzymes (matrix metalloproteinases), expression of a type of collagen (Type X collagen) associated very specifically with cartilage mineralization, and ultimately, apoptosis of the chondrocytes to make way for bone cells to convert the mineralized cartilage into bone. These phenomena characterize the hypertrophic phenotype of chondrocytes, which represents the terminal chondrocyte maturational program resulting in mineralization and cellular apoptosis. PTHrP expression in the growth plate is in turn regulated by another factor, Indian Hedgehog (IHH). This program controls chondrocyte proliferation and hypertrophy at the growth plate but activation of this pathway in articular cartilage is a contributing factor in the pathophysiology of articular cartilage degeneration.

Regulatory factors known to be expressed in the growth plate (e.g., PTHrP, IHH, PTH/PTHrP receptor, matrix metalloproteinase 9 (MMP9), matrix metalloproteinase 13 (MMP13), and bone morphogenetic protein 6 (BMP6)) are absent in normal human adult articular cartilage but are expressed early in cartilage degeneration. Furthermore, PTHrP in osteoarthritic cartilage is expressed in groups of cloning (i.e., proliferating) chondrocytes. Enhanced proteoglycan synthesis also occurs early after cartilage injury, and is also thought to represent a cellular attempt at tissue repair. However, almost invariably, these cellular activities are insufficient to repair the tissue or halt progressive cartilage degeneration. Similar events are observed in various types of cartilage (e.g., articular and meniscal) and other musculoskeletal soft tissues, e.g., skeletal muscle tissue, intervertebral discs, ligaments, and tendons. The methods herein are designed to allow repair and to prevent degeneration of articular cartilage, skeletal muscle, non-articular cartilage (including meniscal cartilage), ligaments, tendons, and intervertebral discs.

The reparative actions of intermittent activation of the PTH/PTHrP receptor in skeletal tissues include stimulation of matrix synthesis, usually collagen and proteoglycans, and cellular proliferation. Mesenchymal stem cells also respond to PTH/PTHrP receptor stimulation and are activated at and/or recruited to sites of musculoskeletal injury to enhance repair of tissues.

The methods include the steps of selecting a subject in need of protection or repair of the selected tissue and administering intermittently to the subject a PTH/PTHrP receptor agonist or a parathyroid releasing factor or stimulus. Intermittent stimulation of the PTH/PTHrP receptor stimulates the mesenchymally derived stem cells in the target tissue but, unlike continuous administration, does not facilitate escape of cells like chondrocytes from the proliferative stage to the hypertrophic state.

The subject in need of cartilage (e.g., articular or meniscal cartilage) protection or repair may have injured cartilage or may be at risk for cartilage degeneration. Cartilage injuries include, but are not limited to, traumatic injury (e.g., an internal derangement, a fracture of an articular surface, blunt injury) and surgical injury (e.g., associated with arthroscopic shaving or abrasion of cartilage, chondroplasty, drilling, meniscus repair, or mosaicplasty). The subject in need of cartilage protection or repair may have a disease or condition or may be at risk for such disease or condition, such as osteoarthritis, infection (e.g., a joint infection), deformity (resulting, e.g., in abnormal joint load), gout, and calcium pyrophosphate deposition disease. Such injuries, diseases or conditions may be associated with a defect in a cartilage or articular surface or may put the subject at risk for degradation of cartilage. For example, one of skill in the art could select a subject in need of cartilage protection or repair based on epidemiological data that the injury, condition or disease is known to be associated with an increased risk of osteoarthritis or may use imaging techniques or other clinical tests to detect a defect in the cartilage. Clinical signs, for example, could include swelling, pain, and joint crepitance or instability.

The PTH/PTHrP receptor agonist is optionally a peptide agonist or a small molecule. Examples of receptor agonists include N-terminal peptides or peptide analogs of PTH or PTHrP. One example of an N-terminal peptide is teriparatide) (FORTEO®) (Eli Lilly and Company; Indianapolis, Ind.).

Also useful in the methods taught herein are agents that stimulate release of PTH. By way of example, calcium receptor blocking drugs function to disrupt normal signaling in the parathyroid glands and to induce a burst of PTH release from the glands. The released PTH, stimulates the PTH/PTHrP receptor as a PTH/PTHrP agonist. The PTH/PTHrP releasing factor is optionally a peptide agonist or small molecule (e.g., ronacaleret, manufactured by GlaxoSmithKline; Philadelphia, Pa.).

Similar methods are useful in the protection and repair of musculoskeletal soft tissues such as non-articular cartilage, ligament, tendon, skeletal muscle (including, e.g., sphincter muscles like the pelvic floor and the urethral sphincter muscle), meniscus, or intervertebral disc. In these tissues, intermittent stimulation of PTH/PTHrP receptor expressing cells can be expected to enhance matrix synthesis, cell proliferation, and activation or recruitment of reparative mesenchymal stem cell. Thus, provided herein is a method for protecting or repairing skeletal muscle, ligament, tendon or intervertebral disc in a subject. Such a method includes the steps of selecting a subject in need of protection or repair of a skeletal muscle, tendon, ligament, or intervertebral disc and administering intermittently to the subject a parathyroid hormone/parathyroid hormone-related protein (PTH/PTHrP) receptor agonist.

As described above with regard to selection of a subject in need of cartilage repair or protection, one of skill in the art can select a subject in need of protection or repair of a muscle, ligament, tendon or intervertebral disc based on epidemiological data, imaging techniques, or clinical signs and symptoms. For example, an intervertebral disc may be herniated or compressed because of surgery, injury, spinal deformity, or arthritis. Disc herniation or compression can be associated with pain and nerve impingement. Furthermore, an injury to the spine (e.g., an athletic injury or automobile injury) could put a subject at risk of developing a degenerative disc disease or condition. Spinal surgery or surgical repair of a herniated disc may also mean a subject is in need of intervertebral disc repair or protection according to the present methods.

Similarly, an injury or surgery could indicate a subject is in need of protection or repair of a tendon or ligament. Stretching or tearing of a tendon or ligament, as evidenced by joint laxity, pain, clinical signs, imaging, or epidemiological data. A subject may be in need of tendon or ligament protection, or stimulation of repair, following trauma to or surgical repair of a tendon or ligament.

Certain diseases and conditions associated with articular cartilage and musculoskeletal soft tissues can be inherited. Genetic diseases that predispose cartilage or musculoskeletal soft tissues to degeneration or damage would include, for example, diseases leading to degeneration of articular cartilage or intervertebral disk degeneration, such as type II collagen mutations, ochronosis, mucopolysaccharidoses, type IX collagen mutations, Cartilage Oligomeric Matrix Protein (COMP) mutations, etc. Genetic disorders affecting ligaments and tendons would include, for example, Ehlers-Danlos syndromes and Marfan syndrome. Additionally, for example, certain forms of arthritis are inherited. Others diseases or conditions associated with articular cartilage and musculoskeletal soft tissues are associated with an acute ischemic event or a chronic ischemic disease or condition.

Optionally, in the methods taught herein, the subject does not have osteoporosis or a bone fracture. However, the methods herein can be combined with various other treatments. For example, the methods can be combined with chondrocyte or mesenchymal stem cell implantation to a joint, or a traumatic or surgically created defect in the articular surface with or without a scaffolding material to retain the implanted cells in place. As another example, chondrocytes or mesenchymal stem cells capable of differentiating into chondrocytes can be implanted into a degenerating intervertebral disc of a subject and the PTH/PTHrP agonist administered intermittently to promote repair by the implanted chondrocytes. Similarly, a tendon or ligament graft can be accompanied by administration of a PTH/PTHrP agonists.

For purposes of the methods taught herein, intermittent administration of the PTH/PTHrP receptor agonist or PTH releasing factor can be performed 1-2 times daily or every two, three, four, five, six or seven days. In some cases, one administration may be sufficient for preventative purposes; but generally, one of skill in the art will determine that multiple treatments are necessary. In certain cases, local administration may be used. For example, when a subject is undergoing surgery, the PTH/PTHrP receptor agonist may be injected into the joint or site of repair. Generally, however, systemic injection will be used to avoid side effects such as infection or swelling.

The agonist or releasing factor can be administered by any route, including oral, rectal, sublingual, ocular, and parenteral administration. Parenteral administration includes, for example, intrathecal, intravenous, intramuscular, intra-arterial, intraperitoneal, intranasal, intravaginal, intraocular, intravesical (e.g., to the bladder), intradermal, transdermal, topical or subcutaneous administration. Also contemplated is the instillation of a drug in the body of the subject in a controlled formulation, with systemic or local release of the drug to occur at a later time. For example, the drug may be localized in a depot at the site of intervention for subsequent release to a local site, e.g., at the site of damage or surgical intervention. Advantageously, the agents are administered in the form of a pharmaceutical composition.

One or more agonists or releasing factors useful in the practice of the methods described herein may be administered simultaneously, by the same or different routes, or at different times during treatment. The compounds may be administered before, along with, or after other medications, including other compounds. For example, the agonists or releasing factors could be administered with anti-inflammatory agents.

The treatment using methods described herein may be carried out for as long a period as necessary, either in a single, uninterrupted session, or in discrete sessions. The treating physician will know how to increase, decrease, or interrupt treatment based on subject's response. Optionally, treatment is carried out 1, 2, 3, 4 weeks; 2, 3, 4, 5, 6, 7, 8, 9, 10, 11, 12 months; 2 years or more. One of skill in the art can monitor the subject for any adverse side-effects, including development of osteosarcoma and for improvement in clinical status and adjust the treatment accordingly. The treatment schedule may be repeated as required.

Also provided herein is a scaffold composite or material comprising mesenchymal stem cells and a PTH/PTHrP receptor agonist (e.g., a peptide agonist or a small molecule as described herein) or a PTH/PTHrP releasing factor (e.g., a peptide agonist or small molecule described herein). Also provided is a scaffold composite or material comprising mesenchymal stem cells treated with a PTH/PTHrP receptor agonists or a PTH/PTHrP releasing factor prior to addition of the cells to the scaffold material or composite. Such scaffolding materials include, for example, a biodegradable scaffolding material designed for insertion into a cartilage defect or defect in a skeletal muscle, intervertebral disc, ligament, or tendon. Examples of scaffold composites and materials and methods of making and using them can be found for example in Abe et al., Tissue Engineering, 10: 585-594 (2004); Orthopedic Tissue Engineering Basic Science and Practices, by Goldberg et al.; published by Informa Health Care (2004); U.S. Pat. Nos. 7,208,177; 6,737,073; 6,530,956; 6,179,871; 5,842,477; 5,624,463; US Patent Application Nos. 20080195211; 20060273279; 20060111778; 20020009477.

Also provided is a method of treating a defect in articular cartilage or musculoskeletal soft tissue (e.g., non-articular cartilage, tendon, ligament, intervertebral disc, or skeletal muscle) in a subject including the steps of inserting into the defect chondrocytes or mesenchymal stem cells and/or a woven or unwoven scaffold material or composite described herein. The scaffold material or composite optionally includes mesenchymal stem cells, chondrocytes, myocytes, fibroblasts, or a combination thereof. Optionally the cells in the scaffold are pretreated with a PTH/PTHrP receptor agonist or a PTH/PTHrP releasing factor. Optionally, the scaffold material contains or is impregnated with a PTH/PTHrP receptor agonist or releasing agent. Alternatively or in addition, the method further comprises either administering to the scaffold or to the subject a PTH/PTHrP receptor agonist or a PTH/PTHrP releasing factor. Optionally, the scaffold contains the PTH/PTHrP receptor agonist or a PTH/PTHrP releasing factor prior to insertion into the defect. Optionally, the PTH/PTHrP receptor agonist or a PTH/PTHrP releasing factor is administered to the subject after insertion of the scaffold, and such administration can be local or systemic and such administration is repeated intermittently as described herein.

Provided herein are uses of the agonist or releasing agent for preparing a medicament for protecting or repairing articular cartilage and musculoskeletal soft tissues such as non-articular cartilage, tendon, ligament, meniscus, intervertebral discs, and skeletal muscle. Further provided is a use of the agonists or releasing factor for protecting or repairing articular cartilage and musculoskeletal soft tissues such as non-articular cartilage, tendon, ligament, intervertebral discs, and skeletal muscle. The compounds may be administered in the form of a pharmaceutical composition, in combination with a pharmaceutically acceptable carrier. The amount of compound in such formulations may comprise from 0.1 to 99.99 weight percent of the composition. Pharmaceutically acceptable carrier means any carrier, diluent or excipient which is compatible with the other ingredients of the formulation and not deleterious to the recipient.

The agonist or releasing factor may be administered with a pharmaceutically acceptable carrier selected on the basis of the selected route of administration and standard pharmaceutical practice. The compound may be formulated into dosage forms according to standard practices in the field of pharmaceutical preparations. See *Remington: The Science and Practice of Pharmacy*, 21$^{st}$ Edition, Lippincott Williams & Wilkins, Philadelphia, Pa. (2005). Suitable dosage forms may comprise, for example, tablets, capsules, solutions, parenteral solutions, troches, suppositories, or suspensions.

For parenteral administration, the compound can be mixed with a suitable carrier or diluent. Various diluents are known such as water, oil (particularly a vegetable oil), ethanol, saline solution, aqueous dextrose (glucose) and related sugar solutions, glycerol, or a glycol such as propylene glycol or polyethylene glycol. One of skill in the art would select a carrier that avoids degradation of the active agent. For example, the carrier can be a water soluble carrier, including, for example, an albumen solution. Solutions for parenteral administration can contain a water soluble salt of the compound. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration can take the form of an aqueous solution, dispersion, suspension, or emulsion.

For oral administration, the compound can be combined with one or more solid inactive ingredients for the preparation of tablets, capsules, pills, powders, granules or other suitable oral dosage forms. For example, the active agent can be combined with at least one excipient such as fillers, binders, humectants, disintegrating agents, solution retarders, absorption accelerators, wetting agents, absorbents, or lubricating agents. According to one tablet embodiment, the active agent can be combined with carboxymethylcellulose calcium, magnesium stearate, mannitol, and starch, and then formed into tablets by conventional tableting methods.

The specific dose of the agonist or releasing agent required to obtain therapeutic benefit in the methods of treatment described herein will, of course, be determined by the particular circumstances of the individual patient including the size, weight, age and sex of the patient, the nature and stage of the condition being treated, and the route of administration of the compound. For example, a daily dosage of teriparatide is generally about 20 µg daily for an adult human, using a subcutaneous injection. Higher or lower doses and alternative means of administration are also contemplated.

The agent may be formulated in a unit dosage form. The term unit dosage form refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions described herein may also be formulated so as to provide slow or controlled release of the compound therein using, for example, hydroxypropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the compound at the required rate to maintain constant pharmacological activity for a desirable period of time. Since the receptor stimulation must be intermittent, however, the controlled-release of the compound may be stimulated by various inducers, for example pH, temperature, enzymes, water, or other physiological conditions or compounds so that the release is intermittent.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

Peptides for use in the pharmaceuticals can be made using various techniques known to one of skill in the art. The term peptide or polypeptide are used interchangeably herein and refers to two or more amino acids linked by a peptide bond. The peptides can be isolated from tissue, cells, or cultures. They can be made by proteolytically cleaving a larger polypeptide or protein, using recombinant technology, or by peptide synthesis methods. By way of example, one of skill in the art can modify and design peptide agonists starting from the known sequences for PTH and PTHrP. The sequence for human parathyroid hormone is MIPAKDMAKVMIVMLAICFLTKSDGKSVKKRSVSE-IQLMH NLGKHLNSME RVEWLRKKLQ DVHN-FVALGA PLAPRDAGSQ RPRKKEDNVL VESHEKSLGE ADKADVNVLT KAKSQ (SEQ ID NO:1) (the first 34 amino acid residues know to bind the PTH/PTHrP receptor are underlined). The sequence for parathyroid hormone-related peptide is MQRRLVQQWS VAVFLLSYAV PSCGRSVEGL SRRLKRAVSE HQLLHDKGKS IQDLRRRFFL HHLI-AEIHTA EIRATSEVSP NSKPSPNTKN HPVRFGSDDE GRYLTQETNK VETYKEQPLK TPGKKKKGKP GKRKEQEKKK RRTRSAWLDS GVTGSGLEGD HLS-DTSTTSL ELDSRRH (SEQ ID NO:2). One of skill in the art, using the N-terminal regions of either peptide can design peptide analogs as well as fragments useful in the methods taught herein. For example, using the first 34 amino acid residues of PTH (MIPAKDMAKV MIVMLAICFL TKS-DGKSVKK RSVS) (SEQ ID NO:3), one of skill in the art can modify one or more amino acid residues by insertion, deletion or substitution. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Useful in the methods provided herein are PTH or PTHrP fragments containing one or more conservative amino acid substitutions. Also useful in the methods are peptides having 80, 90, 95, or 99% sequence identity with the PTH/PTHrP receptor binding region of PTH or PTHrP. Agonistic properties of the peptides can be verified by screening for binding of the peptide to the receptor, by the ability of the peptide to protect or repair cartilage, or by the ability to stimulate chondrocyte proliferation and matrix synthesis.

By intermittent administration is meant a repetitive, non-continuous administration. With regard to intermittent contact between a peptide or small molecule and a receptor, such intermittent exposure occurs when the peptide or molecule is not bound to the receptor for a period of time minutes or hours or days. Thus, intermittent administration of a peptide or small molecule to a subject means that the peptide or small molecule has cleared sufficiently so as not to have a physiological effect on the receptor for a sufficient period of time before a subsequent administration.

By protecting or promoting repair is meant that degradation or deterioration is slowed or decreased in amount or that any deterioration or degradation is reversed in part or in full. Such protection or repair can slow, reduce, or eliminate the clinical symptoms of the condition being treated.

As used herein, a subject includes a mammal such as a primate (e.g., a human), domesticated animal (such as a cat, dog, etc.), livestock (e.g., cattle, horse, pig, sheep, goat, etc.), laboratory animal (e.g., mouse, rabbit, rat, guinea pig, etc.) and bird. The term does not denote a particular age or sex. Thus, adult and newborn subjects, whether male or female, are intended to be covered. As used herein, patient or subject may be used interchangeably and can refer to a subject with a disease or disorder (e.g. osteoarthritis). The term patient or subject includes human and veterinary subjects.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that, while specific reference of each various individual and collective combinations and permutation of these compounds may not be explicitly disclosed, each is specifically contemplated and described herein. Similarly, various steps of a method may be recited but such steps can be performed in each and every combination and permutation of the steps of the regime are specifically contemplated unless specifically indicated to the contrary. Likewise, any subset or combination of these materials, compositions, components, or method steps is also specifically contemplated and disclosed.

Publications cited herein and the material for which they are cited are hereby specifically incorporated by reference in their entireties.

EXAMPLES

Example 1

Immunohistochemical Detection of Chondrocyte Maturation Markers in Cartilage from Normal Subjects and Subjects with Mild or Severe Osteoarthritis Immunohistochemistry was performed on 3-4 micron sections of paraffin embedded cartilage tissue sections from individuals diagnosed with mild or severe osteoarthritis as well as control subjects. The streptavidin-enzyme conjugate method was used. Appropriate fixation and decalcification of was achieved using Immunocal (Decal Chemical Corp.; Tallman, N.Y.). Two xylene rinses were used to remove the paraffin wax from the tissue sections. Deparaffinization and hydration were performed as follows: Xylene for 1-5 minutes, Xylene for 2-5 minutes, 100% Alcohol for 1-3 minutes, 100% Alcohol for 2-3 minutes, 95% Alcohol for 1-3 minutes, 85% Alcohol for 1-3 minutes, 70% Alcohol for 1-3 minutes, and distilled $H_2O$ for 3 minutes. In addition, tissue section microwaving was used for antigenic recovery (antigen "unmasking"). After the tissue sections were deparaffinized and rehydrated, endogenous peroxidase was quenched with 3% hydrogen peroxide for 10 minutes. The slides were rinsed in PBS and then microwaved in 0.01M citrate buffer for 1 minute at power level 6. Afterwards, the slides remained in the hot solution for 30 minutes at room temperature. If a digestion step was necessary, slides were digested according to standard procedures. The slides were then drained and placed in PBS for 5 minutes. PBS was removed and the slides were placed in a humid chamber. Normal serum was applied for 20 minutes to saturate nonspecific binding sites (1:20 dilution).

The primary antibody dilution used was the dilution showing the best staining with the least amount of non-specific background. The primary antibodies were diluted in PBS/BSA and applied to the slides and allowed to incubate at 4° C. overnight. Appropriate controls were run for each immunohistochemical reaction and included control tissue known to express the antigen of interest as a positive control, PBS/BSA, and an irrelevant primary antibody.

At the beginning of day 2, the humid chamber was removed from the refrigerator and placed at room temperature for 1 hour. Each slide was rinsed with PBS, then placed in a rack in a staining dish with PBS for 5 minutes. The slides were removed from PBS, excess PBS was wiped away, the slides were placed in a humid chamber, and the appropriate secondary antibody was applied for 30 minutes at room temperature. The slides were again rinsed in PBS in a staining dish for 5 minutes, drained and the excess liquid was wiped away. The slides were placed in the humid chamber and HRP Streptavidin (1:250 dilution) was applied for 30 minutes. The slides were again rinsed in PBS in a staining dish for 5 minutes, drained and the excess liquid wiped away, placed in the humid chamber, and then AEC Chromagen was applied for 5-10 minutes, according to standard procedures. The slides were drained onto an AEC absorbent pad, then washed in distilled $H_2O$ 2 times for 5 minutes, then dipped into hematoxylin, and rinsed in distilled $H_2O$ until water was clear. The slides were then dipped into ammonia $H_2O$, rinsed several times in distilled $H_2O$, and coverslips were added with aqueous mounting media. The slides were covered and kept away from light to prevent fading of the stain.

Figure 2A:
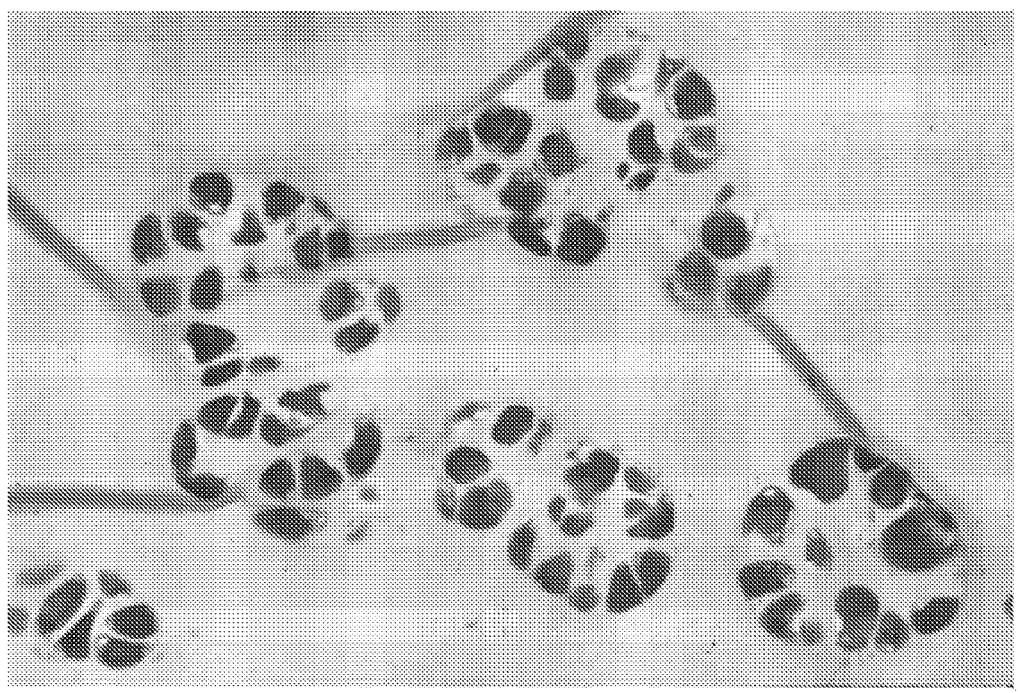
FIG. 2A shows a micrograph showing immunohistochemical labeling of proliferating clones of osteoarthritic human articular cartilage using a parathyroid hormone-related protein (PTHrP) antibody.
Figure 2B:
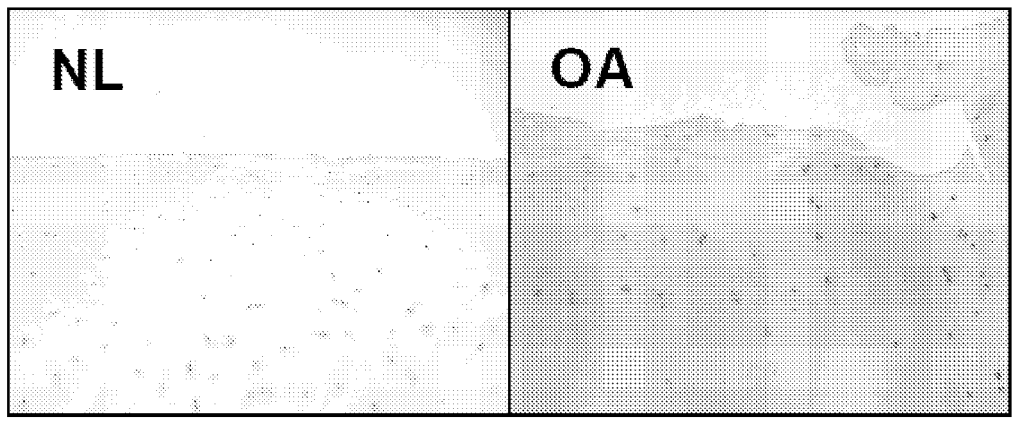
FIG. 2B shows two micrographs, one from a normal human articular cartilage (NL) and one from an osteoarthritic human articular cartilage (OA), showing immunohistochemical labeling using an antibody to the parathyroid hormone/parathyroid hormone-related protein (PTH/PTHrP) receptor.
Figure 3A:
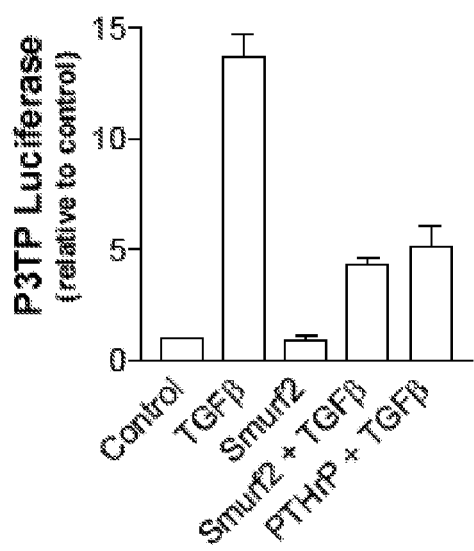
FIG. 3A is a histogram showing expression of p3tp-luciferase levels relative to control (i.e., untreated) in chick sternal chondrocytes cultured with transforming growth factor beta (TGFβ) and transiently transfected with smurf2, alone or in combination, or treated with TGFβ and parathyroid hormone-related peptide (PTHrP) with a chronic exposure for 48 hours.
Figure 3B:
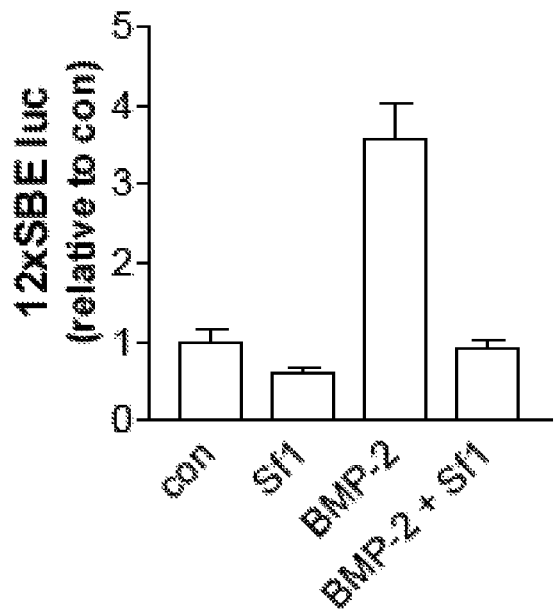
FIG. 3B is a histogram showing expression of a reporter construct containing 12 copies of the Smad 1 binding element upstream of luciferase. Chick sternal chondrocytes containing the reporter construct were cultured and transiently transfected with Smurf1 (Sf1) or treated with exogenously added bone morphogenetic protein-2 (BMP-2) alone or in combination for 48 hours.
Figure 3C:
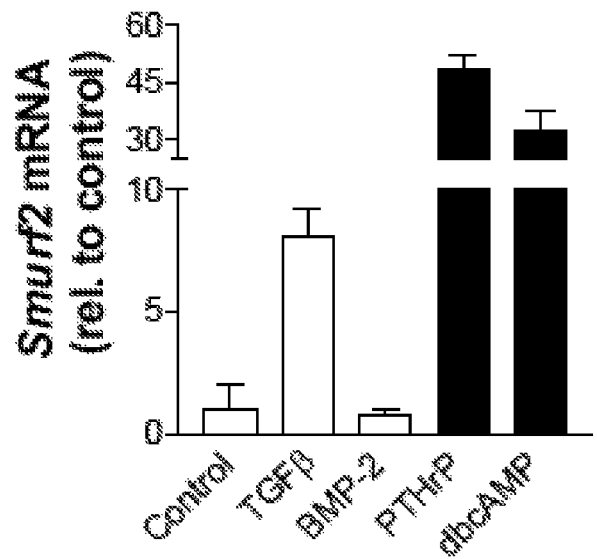
FIG. 3C is a histogram showing levels of Smurf2 mRNA relative to control in chick sternal chondrocytes cultured with TGFβ, BMP-2, PTHrP, or dibutyryl cyclic adenosine monophosphate (dbcAMP) following a chronic, 48 hour exposure.
Figure 3D:
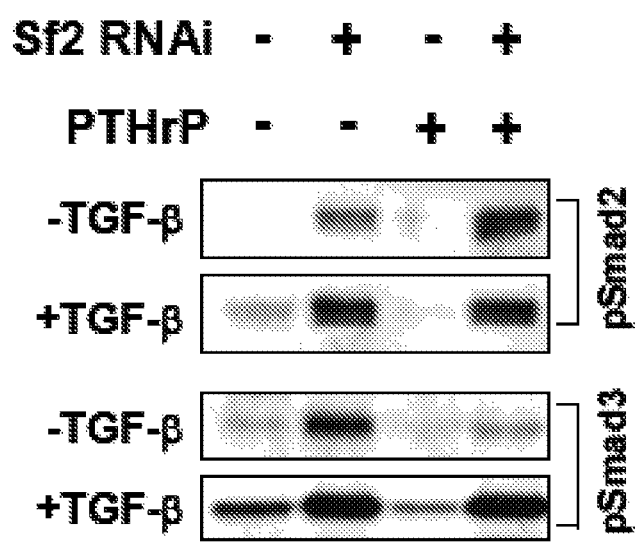
FIG. 3D shows images of Western blots demonstrating that the reduction of pSmad2 and pSmad3 by PTHrP is reversed by inhibiting Smurf2 expression with siRNAs. The Western blots show pSmad3 and pSmad2 levels in chick sternal chondrocytes cultured in the presence or absence of TGFβ, PTHrP and/or a Smurf2 RNAi (Sf2 RNAi) for 48 hours.
Figure 4A:
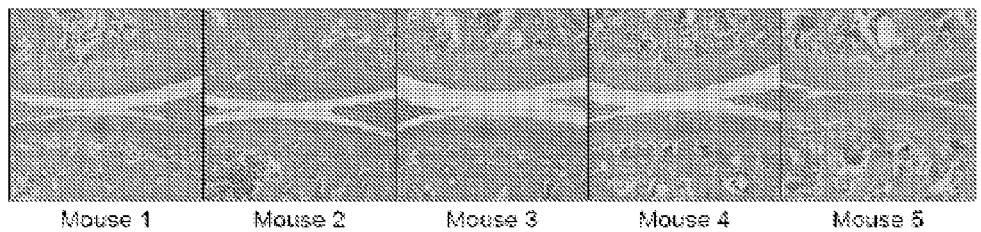
FIG. 4A shows micrographs of mice with a murine injury model and sham mice at 4 weeks following surgery and with 4 weeks of daily treatment with teriparatide.
Figure 4A:
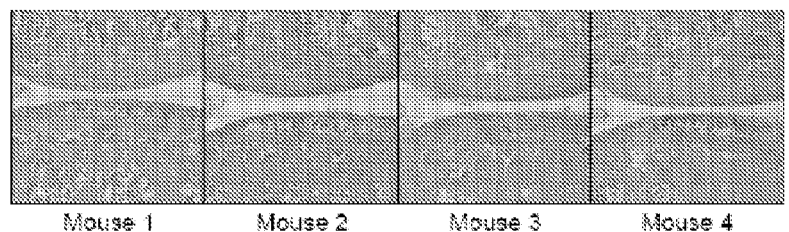
Figure 4A:
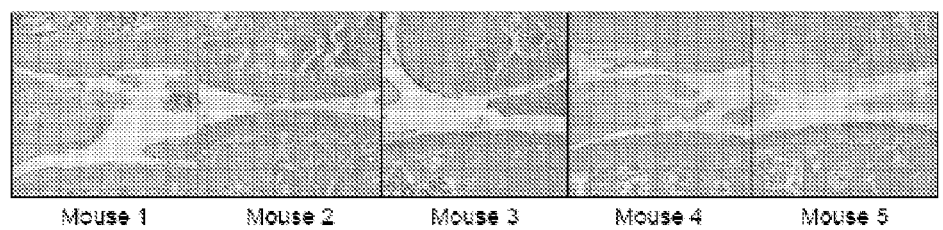
Figure 4A:
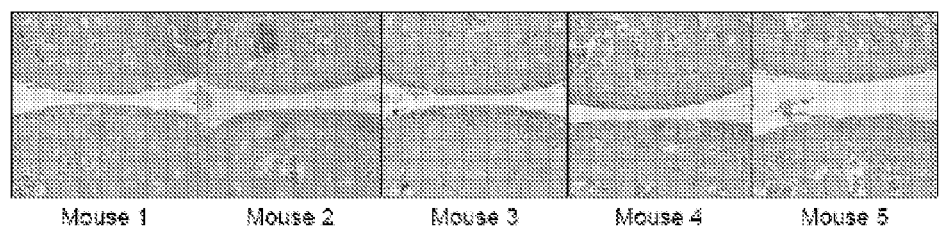
Figure 4B:
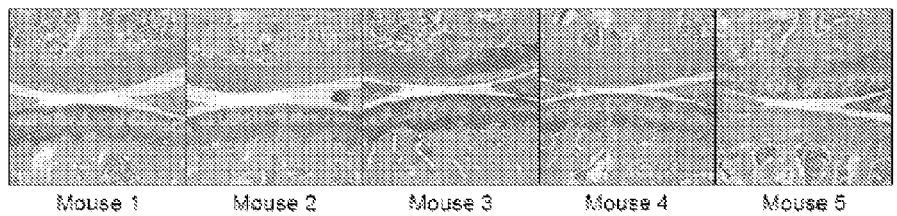
FIG. 4B shows micrographs of mice with a murine injury model and sham mice at 8 weeks following surgery and with 8 weeks of daily treatment with teriparatide.
Figure 4B:
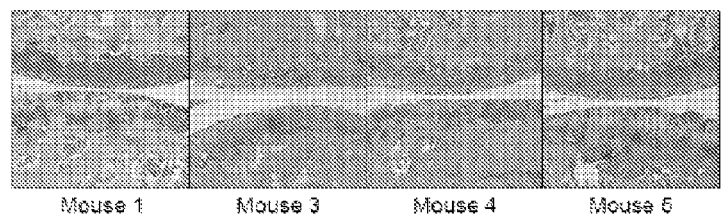
Figure 4B:
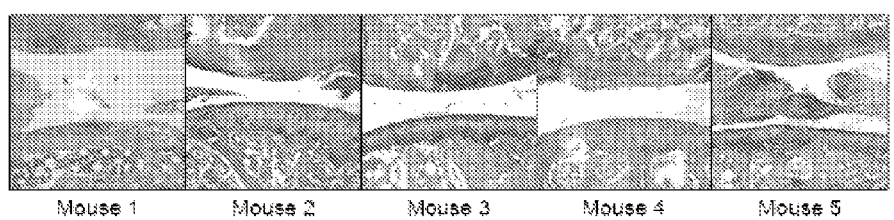
Figure 4B:
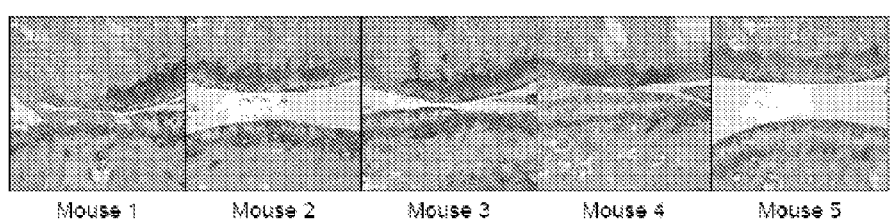
Figure 4C:
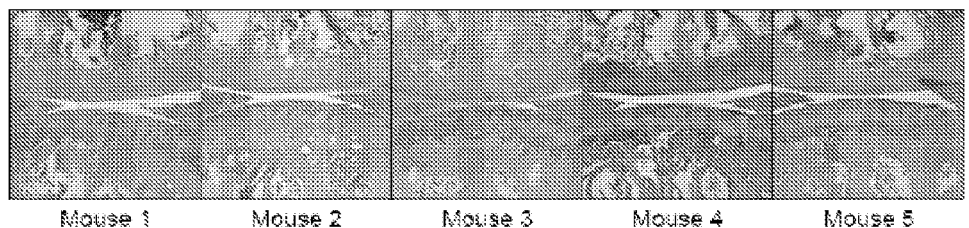
FIG. 4C shows micrographs of mice with a murine injury model and sham mice at 12 weeks following surgery and with 12 weeks of daily treatment with teriparatide.
Figure 4C:
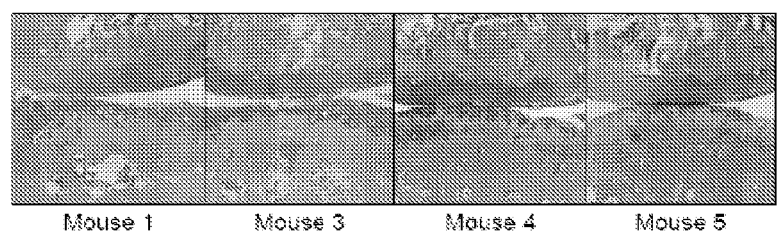
Figure 4C:
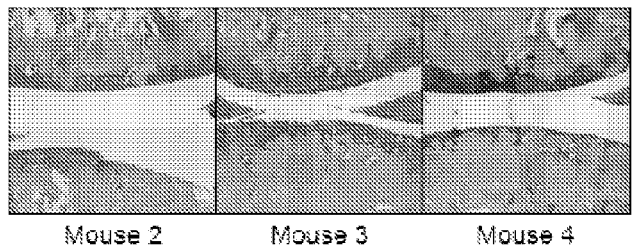
Figure 4C:
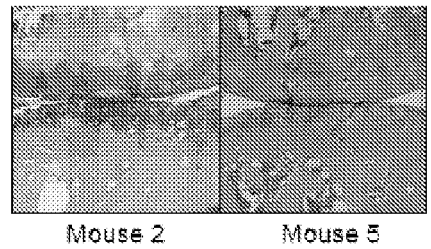

Regulatory factors known to be expressed in the growth plate were absent in normal human adult articular cartilage but were expressed early in cartilage degeneration (FIG. 1), including PTHrP, IHH, PTH/PTHrP receptor, matrix metalloproteinase 9 (MMP9), matrix metalloproteinase 13 (MMP13), Indian Hedgehog (IHH), and bone morphogenetic protein 6 (BMP6). As shown in FIG. 1, chondrocyte maturation markers, such as PTHrP and PTH/PTHrP receptor, were undetectable in normal cartilage but were mildly expressed in mild osteoarthritis (low Mankin score, LM) and are strongly expressed in moderately severe osteoarthritis (high Mankin score, HM). The PTHrP in osteoarthritic cartilage was expressed in groups of cloning (i.e., proliferating) chondrocytes, which is one feature of apparent early attempts of the tissue to repair itself (FIG. 2A). The receptor, PTHR1, was also expressed in osteoarthritic but not normal human articular cartilage (FIGS. 1 and 2B).

Example 2

Effect of Continuous Exposure to PTHrP on Chondrocytes in Culture

PTHrP or dbcAMP stimulated smurf2 expression after 48 hr exposure in chick chondrocytes, suggesting that chronic, continuous (as opposed to intermittent) PTHR1 stimulation enabled escape from maturational suppression by PTHrP and progression of the cells to hypertrophy. Without meaning to be limited by theory, this may have been due to down-regulation of TGF-β signaling by smurf2, allowing BMP signals to drive hypertrophy. Thus, while continuous, longer term stimulation of chondrocytes with PTH or PTHrP upregulated factors such as Smurf2 (FIGS. 3A-3D) that may allow escape from the proliferative to the hypertrophic state by enhancing bone morphogenetic (BMP) signaling, intermittent stimulation of the receptor stimulated cell proliferation and proteoglycan synthesis without turning on the hypertrophic phenotype.

Example 3

Effect of Intermittent Exposure to PTH Fragment 1-34 on Articular Cartilage In Vivo Mice were anesthetized and an arthrotomy of the knee was performed. The medial collateral ligament was surgically transected, and the anterior horn of the medial meniscus was surgically removed to create a mild knee injury. For the severe injury group, the anterior cruciate ligament was also transected, causing severe joint instability in combination with the mild meniscal and medial collateral ligament injuries. The knee was surgically closed and animals were allowed free movement subsequently. One group with the severe combined injuries, as the most difficult case for cartilage protection, was treated daily with injections of teriparatide. After sacrifice at appropriate time points, the knee joints were removed, decalcified, embedded in paraffin, and 4-micron thick sections were stained with Alcian Blue to produce photomicrographs as shown in FIG. 4. The resulting data show that, using an extreme condition of mechanical insult to articular cartilage in mice (transection of the anterior cruciate and medial collateral ligaments plus medial menisectomy of the knee—a condition that causes severe osteoarthritis in both mice and humans), daily injection with teriparatide (FORTEO®; Eli Lily, Indianapolis, Ind.) dramatically retards the development of cartilage degeneration and osteoarthritis (FIG. 4). Teriparatide stimulated cellular repair activities with suppression of hypertrophy or maturational changes.

Example 4

Figure 5:
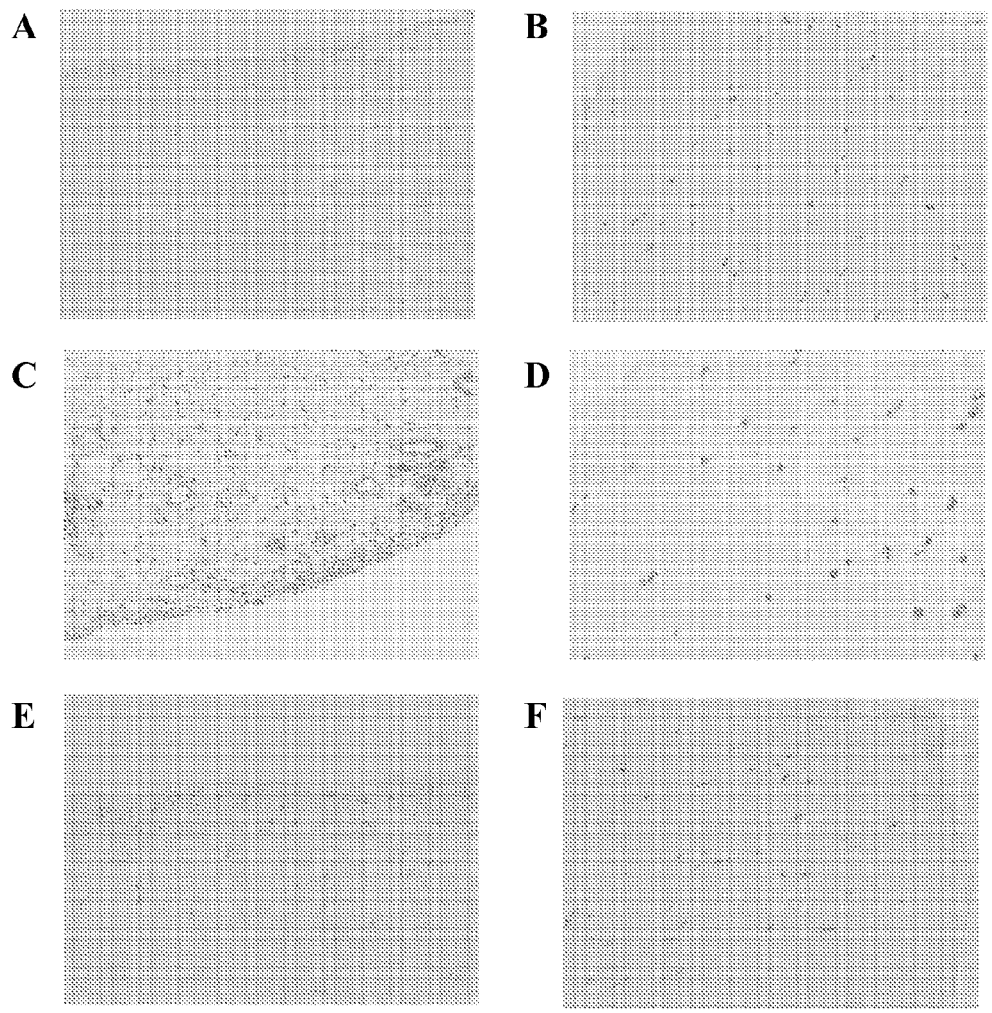
FIG. 5 shows micrographs of normal and injured human meniscus. Panels on the left (5A, 5C, and 5E) show normal samples labeled immunohistochemically with an antibody to PTH/PTHrP receptor, whereas panels on right (5B, 5D, and 5F) show injured meniscus samples. Top panels (5A and 5B) are at 10× magnification; remaining panels (5C-5F) are at 20× magnification. All panels show white zones of the meniscus, except for panel 5C, which shows the red zone of a normal meniscus.

Immunohistochemical Detection of PTH/PTHrP Receptor in Meniscus Cartilage from Normal Subjects and Subjects with Cartilage Injury Immunohistochemistry was performed on human meniscus cartilage from normal and injured subjects. The immunohistochemistry was performed generally as described above, using an antibody that specifically binds PTH/PTHrP receptor. As shown in FIG. 5, the level of PTH/PTHrP is upregulated in injured meniscus (right panels; 5B, 5D, 5F) as compared to normal meniscus (left panels; 5A, 5C, and 5E). The primary antibody used was an anti-PTH/PTHrP receptor (Upstate Cell Signaling Solutions; Lake Placid, N.Y.; Catalog #05-517); the secondary antibody was a biotinylated anti-mouse IgG (H+L) affinity purified made in horse (Upstate Cell Signaling Solutions; Catalog #BA-2000); and normal horse serum was purchased from Vector Laboratories (Burlingame, Calif.; Catalog #S-2000).

Example 5

Figure 6:
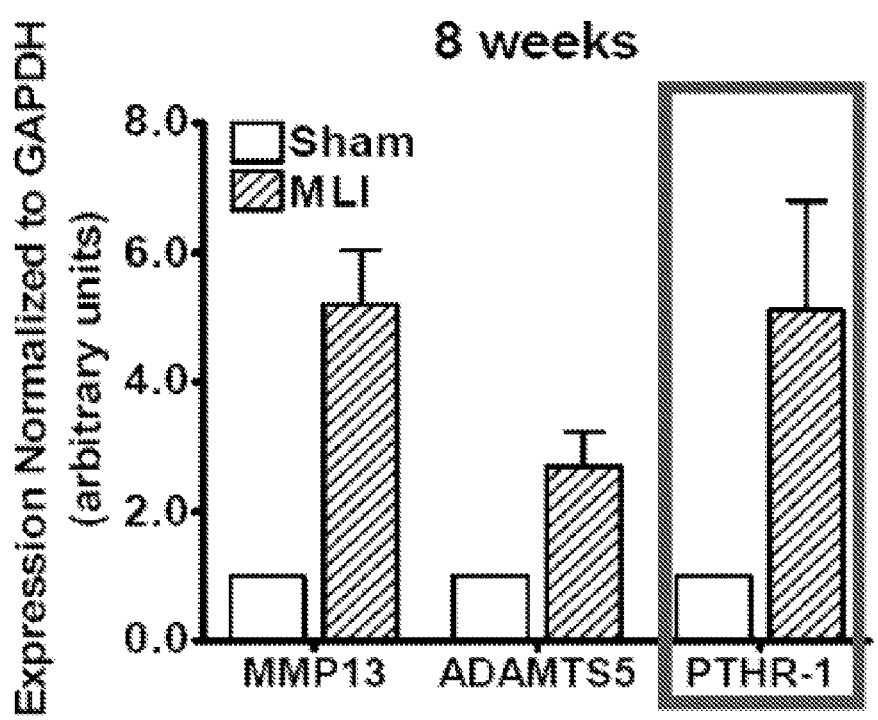
FIG. 6 shows a histogram demonstrating that chondrocyte markers (MMP-13 and ADAMTS5) consistent with osteoarthritis were upregulated in mice with meniscal injury. Additionally, the histogram shows upregulation of PTHR1 in osteoarthritic cartilage in the mice.

Detection of Chondrocyte Maturation Markers in Cartilage from Mice Following Meniscus/Ligament Injury Expression of several chondrocyte markers was determined in mice that had undergone meniscal injury. The expression of MMP13, ADAMTS5, and PTHR-1 was determined and normalized to GAPDH in a control set of mice (sham) and mice that had undergone a meniscus/ligament injury. Chondrocyte maturation markers MMP13 and ADAMTS5 were upregulated in mice that had undergone meniscal injury in comparison to the sham mice (FIG. 6). Further, PTHR1, the target receptor for the parathyroid hormone, was upregulated following meniscal injury (FIG. 6).

Example 6

Figure 7A:
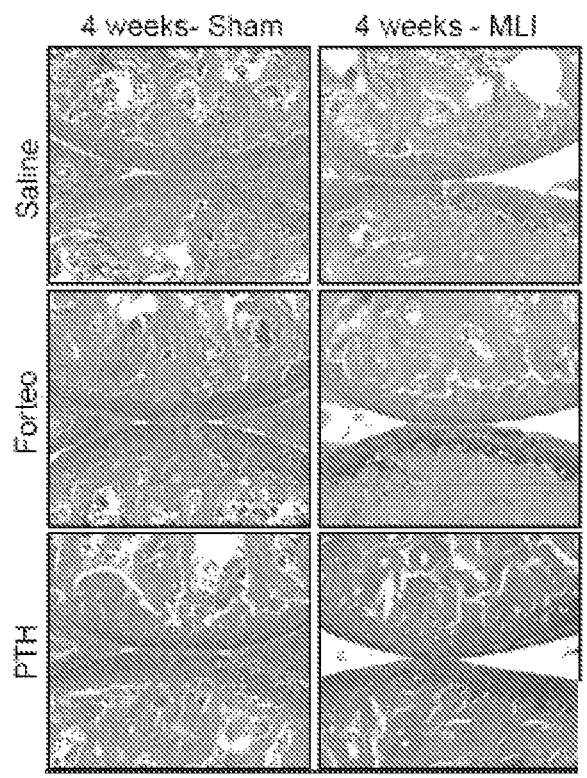
FIGS. 7A and 7B show that daily injection of teriparatide or PTH immediately following sham or meniscus/ligament injury stimulated the production of proteoglycan in the articular cartilage.
Figure 7B:
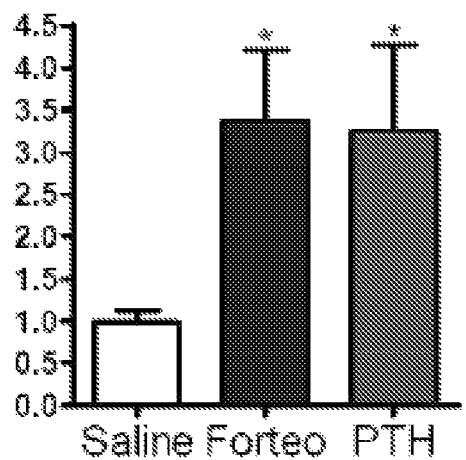

Immediate Treatment with Parathyroid Hormone (PTH) Following Meniscus/Ligament Injury Increases Proteoglycan Abundance and Inhibits Cartilage Loss Mice exposed to sham surgery or meniscus/ligament injury, a model for osteoarthritis, were treated, starting immediately after surgery, with saline, teriparatide, or PTH for 4 weeks. Daily injection of teriparatide or PTH resulted in the upregulation of proteoglycan in the articular cartilage as evidenced by Alcian Blue staining intensity (FIGS. 7A and 7B) demonstrating that PTH has chondroprotective effects and can be used to stimulate PTHR1 and treat subjects with osteoarthritis.

Figure 8A:
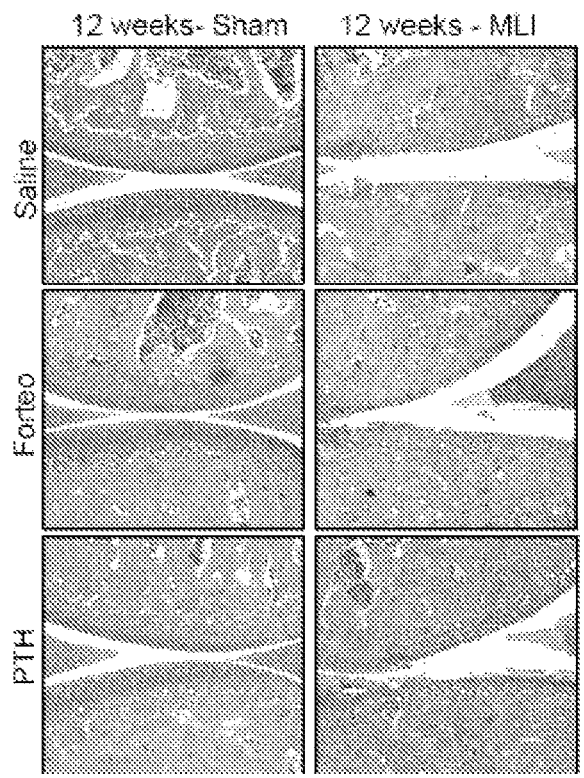
FIGS. 8A and 8B show that immediate treatment with teriparatide and PTH after meniscus/ligament injury for 12 weeks results in a reduction in cartilage loss.
Figure 8B:
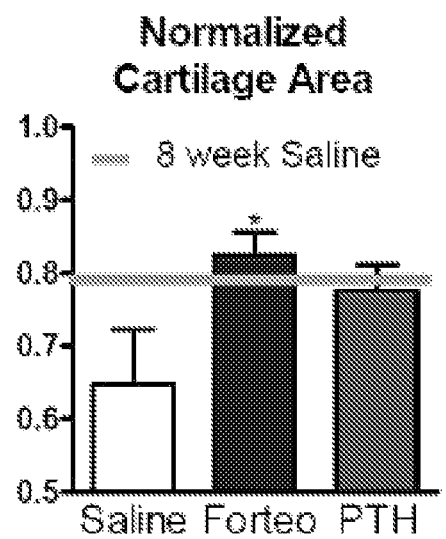

Mice exposed to sham surgery or meniscus/ligament injury were treated, starting immediately after surgery, with saline, teriparatide, or PTH for 12 weeks. Daily injection of teriparatide or PTH for 12 weeks resulted in a reduction in cartilage loss as observed by histomorphometric measurement of joint cartilage area (FIGS. 8A and 8B). These data show the therapeutic effect of PTH in subjects with osteoarthritis as well as the chondroprotective effects of PTH.

Example 7

Figure 9A:
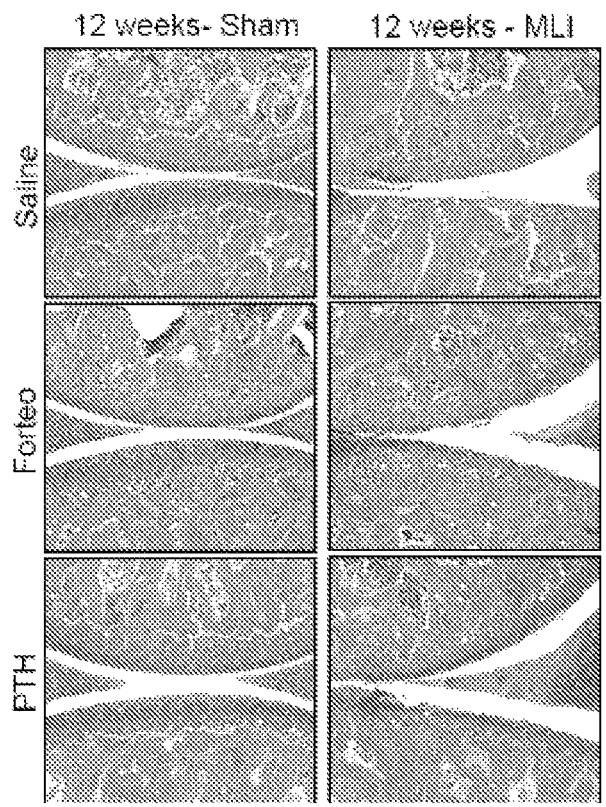
FIGS. 9A and 9B show that delayed treatment with teriparatide and PTH 8 weeks after meniscus/ligament injury results in a reduction in cartilage loss.
Figure 9B:
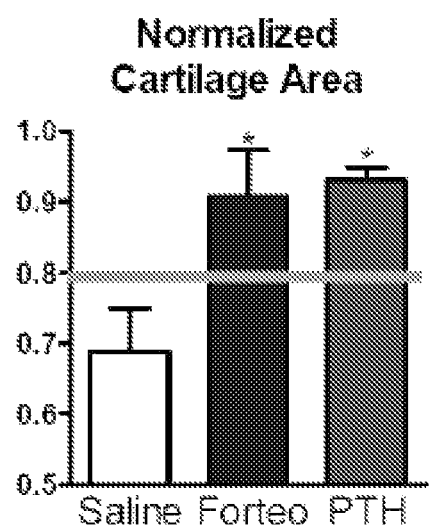

Delayed Treatment of Osteoarthritic Mice with Parathyroid Hormone (PTH) Inhibits Cartilage Loss and Regenerates Lost Cartilage Mice were allowed to develop osteoarthritis for 8 weeks following joint surgery, as described above. After 8 weeks, the mice were treated for 4 weeks with daily injections of teriparatide or PTH, a delayed treatment regimen. A reduction in the loss of cartilage and regeneration of lost cartilage was observed in mice following treatment with teriparatide or PTH for 4 weeks as compared to the saline treated control (FIGS. 9A and 9B). This indicates that PTHR1 receptor stimulation regenerates lost cartilage due to osteoarthritis.

Example 8

Figure 10:
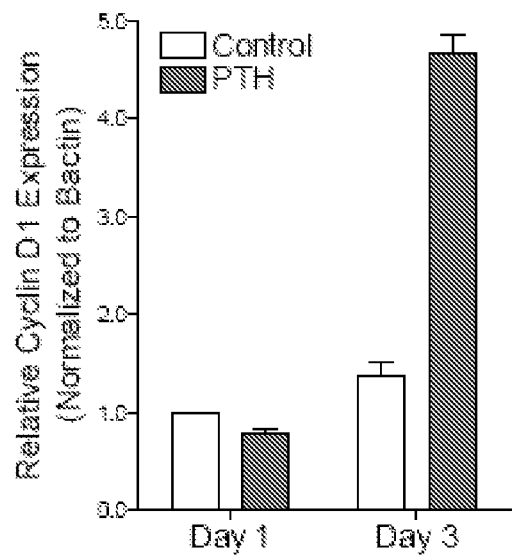
FIG. 10 shows a histogram demonstrating treatment of rabbit mensical cells with PTH for 3 days resulted in an upregulation of cyclin D1 mRNA, indicating a stimulation of meniscal cell proliferation.
Figure 11:
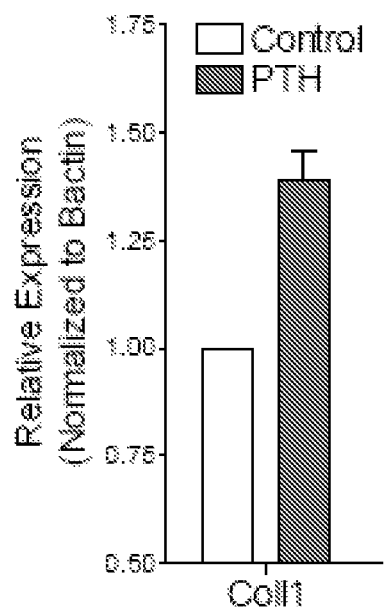
FIG. 11 shows a histogram demonstrating treatment of rabbit meniscal cells with PTH resulted in an upregulation of type I collagen, the predominant matrix molecule in the meniscus, indicating a beneficial effect of PTHR1 stimulation on meniscal healing.

Treatment of Rabbit Meniscal Cells with Parathyroid Hormone (PTH) Simulates Meniscal Cell Proliferation Rabbit meniscal cells were isolated from rabbit menisci and cultured. Cultured meniscal cells were treated with PTH for 1 or 3 days. An upregulation of mRNA for cyclin D1, a marker indicating the stimulation of meniscal proliferation, was observed after 3 days (FIG. 10). This result is consistent with the predicted enhancement of cell proliferation in the meniscus by the stimulation of PTHR1. Also observed was an upregulation of mRNA for type I collagen, the predominant matrix molecule in the meniscus (FIG. 11). This result also shows the beneficial effect of PTHR1 stimulation on meniscal healing.

Figure 12A:
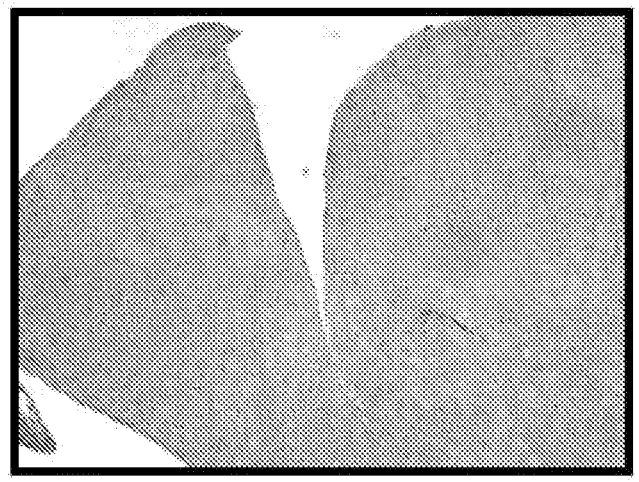
FIGS. 12A and 12B show daily treatment with teriparatide for 4 weeks following meniscal surgery results in preliminary meniscal healing.
Figure 12B:
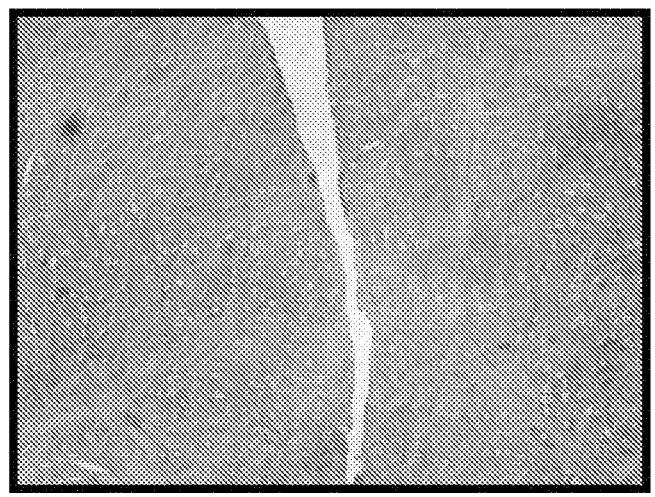

Rabbits underwent surgery to produce white zone meniscal tears. The rabbits were treated with either saline (FIG. 12A) or teriparatide (FIG. 12B) after surgery for 4 weeks. The treated meniscus shows narrowing of the defect with increased cellularity and proteoglycan content (FIG. 12B), which is consistent with a stimulatory healing effect of teriparatide on meniscal healing.

A number of methods have been described. Nevertheless, it will be understood that various modifications may be made without departing from the spirit and scope of the methods described herein.

What is claimed is:

1. A method of promoting repair of articular cartilage in a subject comprising
   a. selecting a human subject with injured articular cartilage; and
   b. administering intermittently to the subject a parathyroid hormone/parathyroid hormone-related protein (PTH/PTHrP) receptor agonist, wherein the cartilage is injured by trauma.

2. The method of claim 1, wherein the PTH/PTHrP receptor agonist is a peptide agonist.

3. The method of claim 2, wherein the peptide agonist is teriparatide.

* * * * *